US00PP15824P3

(12) United States Plant Patent
Coiner

(10) Patent No.: US PP15,824 P3
(45) Date of Patent: Jul. 5, 2005

(54) HYBRID TEA ROSE PLANT NAMED 'INTREPID RED'

(50) Latin Name: *Rosa hybrida*
Varietal Denomination: Intrepid Red

(75) Inventor: James W. Coiner, La Verne, CA (US)

(73) Assignee: Coiner Nursery, LaVerne, CA (US)

( * ) Notice: Subject to any disclaimer, the term of this patent is extended or adjusted under 35 U.S.C. 154(b) by 84 days.

(21) Appl. No.: 10/015,928

(22) Filed: Dec. 5, 2001

(65) Prior Publication Data

US 2003/0106120 P1 Jun. 5, 2003

(51) Int. Cl.[7] ..... A01H 5/00
(52) U.S. Cl. ..... Plt./140
(58) Field of Search ..... Plt./130, 140, 139

*Primary Examiner*—Howard J. Locker
(74) *Attorney, Agent, or Firm*—Christie, Parker & Hale, LLP

(57) ABSTRACT

A new and distinct Hybrid Tea Rose plant variety with dark red flowers.

1 Drawing Sheet

Classification: The present invention relates to a new *Rosa hybrida* plant.

Variety Denomination: The new plant has the varietal denomination 'Intrepid Red'.

BACKGROUND OF THE INVENTION

The present invention relates to a new and distinct variety of rose plant of the hybrid tea rose of the genus *Rosaceae* which was created by crossing as seed and pollen parents two (2) unknown rose varieties. The varietal denomination of the new variety is 'Intrepid Red'.

SUMMARY OF THE INVENTION

Among the novel characteristics possessed by this new variety which distinguishes it from other varieties of which I am aware, is its dark red flowers.

Asexual reproduction by propagation by budding of the new variety as performed in Wasco, Calif. shows that the foregoing and other distinguishing characteristics come true to form and are established and transmitted through succeeding propagations.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of 2-year budded plants of the new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of specimens grown outdoors in Wasco, Calif., during November budded on 'Dr. Huey' understock.

PLANT

Form: Compact.
Growth: Medium vigor.
Size: Height about 48 inches; width about 32 inches.
Foliage:
- *Size.*—Terminal leaflet length about 2 3/16 inches; width about 1¼ inches.
- *Quantity.*—Leaves compound, with 3 to 7 leaflets; most typically 7 leaflets.
- *Color.*—New foliage: Upper side near 136A; under side near 136B. Mature foliage: Upper side near 137A; under side near 137C.
- *Shape.*—Elliptic.
- *Texture.*—Upper side: Smooth, semi-glossy. Under side: Matte.
- *Edge.*—Serrated.
- *Serration.*—Slight.

Petioles: Top surface color near 138B; Under side near 138B.
Stipules: Medium length.
Rachis: Few prickles.
Variegation: None observed.

WOOD

New shoots:
- *Bark.*—Smooth.
- *Wood.*—Near 47B.

Old wood:
- *Bark.*—Smooth.
- *Wood.*—Near 140B.

Flowering stem: Length about 18 to 20 inches.
Winter hardiness: Completely winter hardy.
Preferred growing conditions: Full sun.
Growth habit: Compact.
Leaves per stem: About 5.
Thorns: Average number of thorns and prickles; color of mature thorn near 148D at the tip and near 148C at the base.

FLOWER/INFLORESCENCE

Blooming habit: Continuous.
Bud: Length about 1½ inches; width about 1½ inches.

*Form.*—Classic rose.

*Color.*—Before sepals divide color near 53A; when sepals first divide color near 53B; when petals begin to unfurl color near 53A.

Sepals: Pointed and serrated, usually 5 sepals, occasional extensions about ⅝ inch.

*Size.*—Length in relation to bud, about 1¾ inches.

*Color.*—Topside near 156D; bottom near 138C.

Peduncle:

*Length.*—About 2 inches.

*Aspect.*—Strong, erect.

*Color.*—Near 141D.

Flower:

*Size.*—About 4¼ inches.

*Borne.*—Single — one per stem.

*Form.*—High centered.

Petalage: About 29, petals fan-shaped, petals imbricated, margins smooth.

*Petaloids in center.*—Few, usually about 3, color near 74A.

*Persistence.*—Average.

Fragrance: Slight.

Lasting quality: About 3 weeks on plant; about 7 days after cutting.

Color:

*During first 2 days.*—Inner petals at flower center topside near 60C; bottom near 63A; outer petals topside near 60C, bottom near 63A.

Base of petals (point of attachment): Near 2B.

General tonality from a distance: Near 63A.

Color change: As bloom ages to near 63A; after 3 or more days color near 63A.

Petals:

*Texture.*—Soft.

*Appearance.*—Velvety front; satiny back.

REPRODUCTIVE ORGANS

Arrangement of stamens, filaments and anthers: Regularly arranged around styles, about 50 filaments and anthers, no pollen observed.

Color: Filaments near 5B; Anthers near 6B.

Styles: Medium length.

Hips/seed vessels/ovaries:

*Shape.*—Round.

*Size.*—About ¼ inch.

*Color.*—Near 141C.

Seeds: No seeds.

Disease resistance: The cultivar exhibits average resistance/susceptibility to disease.

I claim:

1. A new and distinct Hybrid Tea Rose plant of the variety substantially as shown and described.

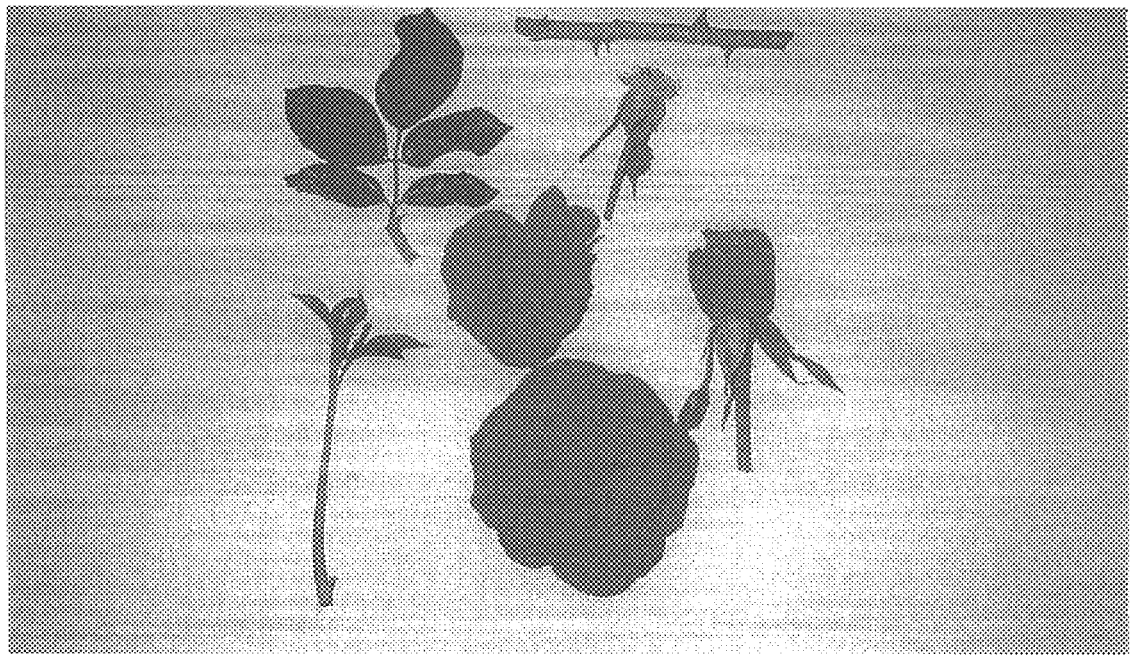

* * * * *